US012767969B2

(12) United States Patent
Yu et al.

(10) Patent No.: US 12,767,969 B2
(45) Date of Patent: Oct. 20, 2026

(54) ENZYME COMPOSITION FOR PREPARING BETA-NICOTINAMIDE MONONUCLEOTIDE, AND APPLICATION THEREOF

(71) Applicant: SHENZHEN READLINE BIOTECH CO., LTD., Shenzhen (CN)

(72) Inventors: Tiemei Yu, Shenzhen (CN); Xiuxiu He, Shenzhen (CN); Guofu Qin, Shenzhen (CN); Ruimei Ling, Shenzhen (CN); Lifeng Lin, Shenzhen (CN); Wenjing Tan, Shenzhen (CN); Junfeng Pan, Shenzhen (CN); Jian Liu, Shenzhen (CN)

(73) Assignee: SHENZHEN READLINE BIOTECH CO., LTD., Shenzhen (CN)

( * ) Notice: Subject to any disclaimer, the term of this patent is extended or adjusted under 35 U.S.C. 154(b) by 391 days.

(21) Appl. No.: 18/555,029

(22) PCT Filed: Sep. 13, 2021

(86) PCT No.: PCT/CN2021/117960

§ 371 (c)(1),
(2) Date: Oct. 12, 2023

(87) PCT Pub. No.: WO2022/217827

PCT Pub. Date: Oct. 20, 2022

(65) Prior Publication Data

US 2024/0279699 A1 Aug. 22, 2024

(30) Foreign Application Priority Data

Apr. 14, 2021 (CN) ......................... 202110397619.0

(51) Int. Cl.
*C12P 19/30* (2006.01)
*C12N 9/10* (2006.01)
*C12N 9/12* (2006.01)

(52) U.S. Cl.
CPC ............ *C12P 19/30* (2013.01); *C12N 9/1077* (2013.01); *C12N 9/1205* (2013.01); *C12Y 204/02001* (2013.01); *C12Y 207/01022* (2013.01)

(58) Field of Classification Search
None
See application file for complete search history.

(56) References Cited

U.S. PATENT DOCUMENTS

| | | | | |
|---|---|---|---|---|
| 10,913,965 | B2 * | 2/2021 | Lawrence ................. | A61P 3/06 |
| 2017/0121746 | A1 | 5/2017 | Velasquez | |
| 2020/0010834 | A1 | 1/2020 | Novick et al. | |
| 2021/0246476 | A1 | 8/2021 | Zhang | |

FOREIGN PATENT DOCUMENTS

| | | | |
|---|---|---|---|
| CN | 1111061 | A | 11/1995 |
| CN | 111748537 | A | 10/2020 |
| CN | 112359082 | A | 2/2021 |
| CN | 112601543 | A | 4/2021 |
| CN | 112795606 | A | 5/2021 |
| CN | 112980906 | A | 6/2021 |
| EP | 3690057 | A1 | 8/2020 |
| WO | 9516785 | A1 | 6/1995 |
| WO | 2018211028 | A1 | 11/2018 |
| WO | 2020014047 | A1 | 1/2020 |

OTHER PUBLICATIONS

Marinescu, George Catalin; et al; "β-nicotinamide mononucleotide (NMN) production in *Escherichia coli*" Scientific Reports, 8, 12278, 2018 (Year: 2018).*

Gossman, Toni I; et al; "NAD + biosynthesis and salvage—a phylogenetic perspective" The FEBS Journal, 279, 3355-3363, 2012 (Year: 2012).*

Japanese first Office Action issued on Oct. 8, 2024 for the Japanese counterpart application No. 2023-563927.

The European Search Report issued on May 19, 2025 for the European counterpart application No. 21936697.8.

International Search Report for PCT/CN2021/117960 mailed Dec. 29, 2021, ISA/CN.

Beata Wielgus-Kutrowska et al., Nicotinamide Riboside, an Unusual, Non-Typical, Substrate of Purified Purine-Nucleoside Phosphorylases, European Journal of Biochemistry, Jan. 15, 1997.

Australian First Office Action issued on Mar. 28, 2025 for the Australian counterpart application No. 2021440288.

Dong, WR., Sun, CC., Zhu, G et al. New function for *Escherichia coli* xanthosine phophorylase (xapA): genetic and biochemical evidences on its participation in NAD+ salvage from nicotinamide. BMC Microbiol 14, 29 (2014).

* cited by examiner

*Primary Examiner* — David W Berke-Schlessel
(74) *Attorney, Agent, or Firm* — Yue (Robert) Xu; Apex Attorneys at Law, LLP

(57) ABSTRACT

The present invention relates to the field of biotechnologies. Disclosed are an enzyme composition for preparing β-nicotinamide mononucleotide (NMN), and an application thereof. In the present invention, by using adenosine and nicotinamide as raw materials, D-ribose 1-phosphate and a nicotinamide ribose intermediate are generated under enzyme catalysis of an enzyme composition of a PNP enzyme and an NRK enzyme, and finally NMN is obtained; only two enzymes need to be involved in the whole reaction system, and the by-product adenine can be recycled. Moreover, only one molecule of ATP needs to be consumed for generating one molecule of NMN, thereby greatly reducing the process cost. The reaction of synthesizing NMN by NRK enzyme catalysis in the last step is irreversible, and thus, the substrate conversion rate can be greatly improved and the production cost can be further reduced.

4 Claims, No Drawings

Specification includes a Sequence Listing.

ENZYME COMPOSITION FOR PREPARING BETA-NICOTINAMIDE MONONUCLEOTIDE, AND APPLICATION THEREOF

The present application is the national phase of International Application No. PCT/CN2021/117960, titled "ENZYME COMPOSITION FOR PREPARING β-NICOTINAMIDE MONONUCLEOTIDE, AND APPLICATION THEREOF", which claims the priority of Chinese Patent Application No. 202110397619.0, filed with the China National Intellectual Property Administration on Apr. 14, 2021, and titled with "ENZYME COMPOSITION FOR PREPARING β-NICOTINAMIDE MONONUCLEOTIDE, AND APPLICATION THEREOF", the entire disclosures thereof are incorporated herein by reference.

FIELD

The present invention relates to the field of biotechnology, specifically to an enzyme composition for preparing β-nicotinamide mononucleotide and uses thereof.

BACKGROUND

β-Nicotinamide mononucleotide (abbreviated as NMN) is a substance present in organisms. Once adenylated by nicotinamide nucleotide adenosyltransferase, it is converted into nicotinamide adenine dinucleotide (NAD+, also known as coenzyme I), an important substance necessary for the survival of biological cells. A study published in Science by David Scinclair's research team in March 2017 showed that the increase in NAD+ in mice reversed the signs of tissue and muscle aging in older mice, suggesting the possibility of human rejuvenation. Due to its large molecular weight, NAD+ cannot be ingested into cells by oral administration, and instead primarily relies on cellular synthesis with low levels. However, recent research on NMN, a small molecule precursor of NAD+, has discovered that consuming β-NMN can significantly increase NAD+ levels in the body and significantly inhibit age-related metabolism, making β-NMN a "miracle drug of youth". To date, nicotinamide mononucleotide has been demonstrated to have a range of medical and healthcare applications, such as the delay of aging, treatment of senile conditions like Parkinson's disease, regulation of insulin secretion, and modulation of mRNA expression.

At present, the main methods for synthesizing NMN include chemical synthesis and biocatalysis. Among them, chemical methods are high in cost and cause serious environmental pollution, so they have been gradually replaced by biocatalytic methods. In comparison, bioenzymatic catalytic production of NMN is more efficient, cost-effective, and eco-friendly. Three biocatalytic methods are currently being used for NMN production. The first one uses nicotinamide ribose as a raw material and generates NMN under the supply of ATP through nicotinamide riboside kinase (EC 2.7.1.22). The second one uses nicotinamide, ribose and ATP as substrates to generate NMN through a reaction catalyzed by D-ribokinase (EC2.7.1.15), ribose phosphate pyrophosphokinase (EC2.7.6.1), and nicotinamide phosphoribosyltransferase (EC.2.4.2.12). The third method uses adenosine or AMP, ATP, and nicotinamide as raw materials to generate NMN through a reaction catalyzed by adenosine kinase (EC 2.7.1.20) (not required when AMP is used as raw material), adenine phosphoribosyltransferase (EC 2.4.2.7) and nicotinamide phosphoribosyltransferase (EC.2.4.2.12).

The above first method uses nicotinamide ribose directly as a raw material and has a high substrate conversion rate, but nicotinamide ribose is expensive and has no cost advantage. The second and third methods both use PRPP and nicotinamide to prepare NMN through nicotinamide phosphoribosyltransferase (EC.2.4.2.12). Because nicotinamide phosphoribosyltransferase catalyzes a reversible reaction, it can also hydrolyze NMN while synthesizing NMN, leading to a low reaction conversion rate. In addition, the intermediate PRPP compound is unstable and is not conducive to the reaction. Furthermore, both methods require ATP to participate in several reaction steps, resulting in a high consumption of ATP throughout the process, and thus the production cost of this biocatalytic method is still high. It is necessary to develop a more efficient and low-cost new method for the biocatalytic preparation of NMN.

SUMMARY

In view of this, an object of the present invention is to provide an enzyme composition for preparing β-nicotinamide mononucleotide (NMN), so that when synthesizing β-nicotinamide mononucleotide with adenosine and nicotinamide as raw materials, 1 molecule of NMN can be generated with only 1 molecule of ATP consumed, and the final step of the reaction to synthesize NMN is irreversible, which can greatly improve the substrate conversion rate and reduce production costs.

Another object of the present invention is to provide a method for synthesizing NMN using the above enzyme composition and to provide related uses of the above enzyme composition in synthesizing NMN.

In order to achieve the above objects, the present invention provides the following technical solutions:

An enzyme composition for preparing β-nicotinamide mononucleotide, comprising purine nucleoside phosphorylase (abbreviated as PNP enzyme) with an EC number of EC 2.4.2.1 and nicotinamide riboside kinase (abbreviated as NRK enzyme) with an EC number of EC 2.7.1.22.

In view of the many defects of the current enzymatic catalysis method, the present invention employs enzymatic reaction technology to provide an alternative process for synthesizing β-nicotinamide mononucleotide using adenosine and nicotinamide. The reaction process is as follows:

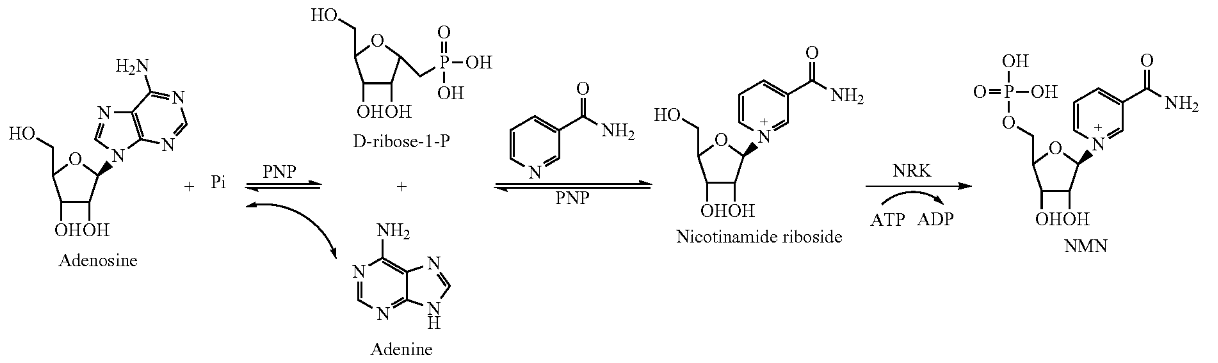

Adenosine and phosphate first synthesize D-ribose-1-phosphate under the action of PNP enzyme, then continue to synthesize nicotinamide ribose with nicotinamide under the catalysis of this enzyme, and then consumes one molecule of ATP for an irreversible reaction to generate NMN under the catalysis of NRK enzyme.

In the above reaction process, the PNP enzyme is a purine nucleoside phosphorylase derived from the group consisting of calf spleen, *Bos taurus, Escherichia coli, Salmonella typhimurium, Bacillus cereus, Bacillus clausii, Aeromonas hydrophila, Bovine Salmonella enterica, Bacteroides fragilis, Deinococcus radiodurans, Aeromonas hydrophila*, and a combination thereof. Preferably, the PNP enzyme is a purine nucleoside phosphorylase derived from the group consisting of calf spleen, *Bos taurus* (Bovine), *Escherichia coli* K12, *Salmonella typhimurium* (strain ATCC 700720), *Bacillus cereus* (strain ATCC 14579), *Bacillus clausii* (strain KSM-K16), *Aeromonas hydrophila, Bovine Salmonella enterica, Bacteroides fragilis* (strain ATCC 25285), *Deinococcus radiodurans* (strain ATCC 13939), *Aeromonas hydrophila*, and a combination thereof.

The present invention requires the participation of PNP enzyme to generate D-ribose-1-phosphate and nicotinamide ribose. The process of generating D-ribose-1-phosphate does not limit the source of PNP enzyme, as long as it belongs to PNP enzyme of EC 2.4.2.1. The process of generating nicotinamide ribose requires specific PNP enzyme to be completed, and the PNP enzymes provided in the present invention are able to complete the two-step reaction.

The NRK enzyme is derived from the group consisting of *B. pseudomallei, Ashbya gossypii, Haemophilus influenzae, Saccharomyces cerevisiae, Schizosaccharomyces pombe, Salmonella typhimurium, Cupriavidus metallidurans, Xanthomonas campestris* pv. *Campestris, Agrobacterium vitis, Pseudarthrobacter chlorophenolicus, Actinobacillus succinogenes, Homo sapiens, Saccharomyces cerevisiae, Ashbya gossypii*, and a combination thereof. Preferably, the NRK enzyme is derived from the group consisting of *B. pseudomallei* K96243, *Ashbya gossypii* ATCC 10895, *Haemophilus influenzae* ATCC 51907, *Saccharomyces cerevisiae* ATCC 204508, *Schizosaccharomyces pombe* ATCC 24843, *Salmonella typhimurium* (strain ATCC 700720), *Cupriavidus metallidurans* (strain ATCC 43123), *Deinococcus radiodurans* (strain ATCC 13939), *Xanthomonas campestris* pv. *Campestris* (strain ATCC 33913), *Agrobacterium vitis* (strain ATCC BAA-846) (*Rhizobium vitis* (strain S4)), *Pseudarthrobacter chlorophenolicus, Actinobacillus succinogenes* (strain ATCC 55618), *Homo sapiens* (Human), *Saccharomyces cerevisiae* (strain ATCC 204508) (Baker's yeast), *Ashbya gossypii* (strain ATCC 10895), and a combination thereof.

The enzyme composition for preparing β-nicotinamide mononucleotide provided by the present invention uses adenosine and nicotinamide as raw materials to synthesize NMN by PNP enzyme and NRK enzyme. Only two enzymes are required to obtain NMN. The raw materials of adenosine and nicotinamide are low in cost, and the by-product adenine can be recycled and reused, significantly reducing costs. In addition, only one molecule of ATP is consumed to generate one molecule of NMN, which greatly reduces the cost. What is even more different from the conventional enzyme catalysis method is that the final reaction of the synthesis of NMN catalyzed by NRK enzyme is irreversible, which can greatly increase the substrate conversion rate and further reduce production costs.

Therefore, the present invention also provides use of the enzyme composition in the manufacture of an enzyme preparation for synthesizing β-nicotinamide mononucleotide or in the synthesis of β-nicotinamide mononucleotide.

Depending on the use, the present invention also provides a method for synthesizing β-nicotinamide mononucleotide by enzymatic catalysis, comprising using adenosine, nicotinamide, ATP, an ion selected from the group consisting of Mg ion and Mn ion, and phosphate as raw materials, and synthesizing β-nicotinamide mononucleotide and phosphate under enzymatic catalysis of the enzyme composition of the present invention. The phosphate can be recycled and used in the next reaction process. The reaction can generally be carried out in a buffer, such as Tris or PBS buffer. For convenient and efficient reaction, PBS buffer can be used as both the reaction medium and the phosphate in the reaction to start the reaction.

Preferably, magnesium ions or manganese ions as coenzyme factors can be provided by one or more of magnesium chloride, magnesium sulfate, magnesium sulfite, magnesium nitrate, manganese chloride, manganese sulfate, and manganese nitrate.

Preferably, the enzyme composition participates in the enzymatic catalysis in the form of a host cell expressing each enzyme, enzyme liquid of each enzyme, or immobilized enzyme of each enzyme. In a specific embodiment of the present invention, the host cell expressing each enzyme is *Escherichia coli* comprising a vector expressing each enzyme. The vector can separately express one of the two enzymes or co-express the two enzymes. The specific preparation process is as follows:

The strain DNA is extracted as a template, and the DNA fragment of the target PNP enzyme or NRK enzyme is amplified by PCR, which can be optimized according to the codon preference of *E. coli*. Table 1 of the present invention lists the sequences of the PNP enzyme or NRK enzyme used in specific examples. The amplified gene is digested based on the restriction site, and linked to a vector plasmid digested with the same enzyme. The plasmid with correct sequence verified by sequencing is transformed into the *E. coli* BL21 (DE3) strain, cultured in LB culture medium, and then induced to expression under IPTG conditions to collect wet cells of each enzyme. The vector plasmid is the commercially available pET28a plasmid, and the amplification primers for each enzyme can be designed according to the coding sequence of each enzyme.

In a specific embodiment of the present invention, the enzyme liquid of each enzyme is an enzyme liquid extracted from a host cell expressing each enzyme. The method is to crush the collected wet cells under high pressure and centrifuge at high speed to collect the supernatant containing crude protein. The liquid is an enzyme liquid containing enzyme, and the supernatant can also be further purified.

Preferably, the method of the present invention also comprises a purification step of β-nicotinamide mononucleotide.

After filtration, separation by chromatography, concentration for crystallization and drying, pure β-nicotinamide mononucleotide is obtained.

The method for generating NMN of the present invention has a substrate conversion rate (calculated as adenosine, a molar ratio of product to adenosine) of 90-99%, and an NMN purity of more than 99%.

It can be seen from the above technical solution that the present invention uses adenosine and nicotinamide as raw materials to generate D-ribose-1-phosphate and nicotinamide ribose intermediate under the enzymatic catalysis of the enzyme composition of PNP enzyme and NRK enzyme, and finally obtains NMN. The entire reaction system only requires the participation of two enzymes, and the by-product adenine can be recycled and reused. In addition, only one molecule of ATP is consumed to generate one molecule of NMN, which greatly reduces the process cost. The final reaction of the synthesis of NMN catalyzed by NRK enzyme is irreversible, which can greatly increase the substrate conversion rate and further reduce production costs.

DETAILED DESCRIPTION

The present invention discloses an enzyme composition for preparing β-nicotinamide mononucleotide and uses thereof. Those skilled in the art can learn from the content of the present invention and appropriately improve the process parameters for achievement. It should be noted that all similar replacements and modifications are obvious to those skilled in the art, and they are deemed to be included in the present invention. The enzyme composition and use thereof of the present invention have been described through preferred examples. Those skilled in the art can obviously make modifications or appropriate changes and combinations to the enzyme composition and use thereof of the present invention without departing from the content, spirit and scope of the present invention to implement and apply the technology of the present invention.

The synthesis method of the present invention and the schematic diagram of its reaction principle are intended to clearly describe the core reaction route, and do not limit whether the entire reaction can be carried out in one step or in multiple steps.

Each enzyme used in the present invention can be artificially synthesized according to the sequence, or can be induced to expression with a plasmid vector according to the method provided by the present invention to load expression gene of each enzyme and induce expression with the help of host cells.

When performing immobilization, the conventional preparation methods of immobilized enzymes in this field can be referred to. In a specific embodiment of the present invention, the present invention uses LX-1000EP epoxy resin (Sunresin, Xi'an) for one-time mixing and immobilization. The immobilization method is as follows: adding 100 ml of the above PNP pure enzyme liquid and 10 ml of NRK pure enzyme liquid to 1 L of potassium phosphate buffer (1M pH 7.5), mixing well, adding 80 g of LX-1000EP epoxy resin, stirring at room temperature for 8 h, filtering to obtain the resin, washing three times with 25 mM pH 8.0 potassium phosphate buffer, and performing suction filtration to obtain the immobilized enzyme. The immobilized enzyme was measured to have a PNP enzyme activity of 800 U/g and an NRK enzyme activity of 80 U/g.

According to the reaction route of the process of the present invention, the amount of each reaction substance can be adjusted based on the actual situation. For maximized efficiency, the present invention provides the following concentrations and amounts of each reaction substance:

The ratio of PNP enzyme to NRK enzyme is calculated as enzyme activity. The enzyme activity ratio of PNP:NRK is 1:(0.01-100), preferably 1:(0.1-10). The substrate concentration of adenosine is 1-150 mM, the substrate concentration of nicotinamide is 1-150 mM, the substrate concentration of ATP is 1 mM-150 mM, the concentration of magnesium ion or manganese ion is 5 mM-200 mM, and the concentration of phosphate salt or Tris is 5-200 mM.

During the reaction process, the pH of the reaction solution is maintained 6.5-9.5, preferably 7.0-8.5; and the reaction temperature is 25-50° C., preferably 35-45° C.

For relevant information on enzymes used in specific examples of the present invention, see Table 1 and Table 2.

TABLE 1

PNP enzyme sequence listing

| corresponding example | Uniprot ID | Source | Gene sequence |
|---|---|---|---|
| Example 1 | Q68719 | *Bos taurus* (Bovine) | MANGYTYEDYQDTAKWLLSHTEQRPQVA<br>VICGSGLGGLVNKLTQAQTFDYSEIPNFPE<br>STVPGHAGRLVFGILNGRACVMMQGRFH<br>MYEGYPFWKVTFPVRVFRLLGVETLVVTN<br>AAGGLNPNFEVGDIMLIRDHINLPGFSGEN<br>PLRGPNEERFGVRFPAMSDAYDRDMRQK<br>AHSTWKQMGEQRELQEGTYVMLGGPNFE<br>TVAECRLLRNLGADAEGMSTVPEVIVARH<br>CGLRVFGFSLITNKVIMDYESQGKANHEE<br>VLEAGKQAAQKLEQFVSLLMASIPVSGHT<br>G<br>as shown in SEQ ID NO. 1 |
| Example 2 | P45563 | *Escherichia coli* (strain K12) | MSQVQFSHNPLFCIDIIKTYKPDFTPRVAFI<br>LGSGLGALADQIENAVAISYEKLPGFPVST<br>VHGHAGELVLGHLQGVPVVCMKGRGHFY<br>EGRGMTIMTDAIRTFKLLGCELLFCTNAA<br>GSLRPEVGAGSLVALKDHINTMPGTPMVG<br>LNDDRFGERFFSLANAYDAEYRALLQKVA<br>KEEGFPLTEGVFVSYPGPNFETAAEIRMMQ<br>IIGGDVVGMSVVPEVISARHCDLKVVAVS<br>AITNMAEGLSDVKLSHAQTLAAAELSKQN<br>FINLICGFLRKIA<br>as shown in SEQ ID NO. 2 |
| Example 2 | Q5WAQ8 | *Bacillus clausii* (strain KSM-K16) | MTEFKQTPHINAKGEIAETVLLPGDPLRAK<br>FIAERFLTDVVQFNSVRNMFGFTGTYNGK<br>RISVMGTGMGMPSMGIYSYELIHVFGVKN<br>LIRVGSCGALQDDLNLYDVILGMGASTNS |

TABLE 1-continued

PNP enzyme sequence listing

| corresponding example | Uniprot ID | Source | Gene sequence |
|---|---|---|---|
| | | | NYVNQYHLPGTFAPLASYSLLEKAKKAAD<br>EKGVPVHVGNILSSDTFYNADEDAAGKW<br>RDMGILGIEMEAAALYMNAAQAGVNALC<br>ILTVSDHIFKEEETTAEERETSFTNMMEIAL<br>ELA<br>as shown in SEQ ID NO. 3 |
| Example 3 | Q5LG76 | *Bacteroides fragilis* (strain ATCC 25285) | MKKYFPSSELIINEDGSVFHLHVKPEWLAD<br>KVILVGDPRGRVALVASHFENKECEVESREF<br>KTVTGTYKGKRITVVSTGIGCDNIDINNNE<br>LDALANIDFQTREEKEHLRSLELVRIGTCG<br>GLQPNTPVGTFVCSEKSIGFDGLLNFYAGR<br>NAVCDLPFERAFLNHMGWSGNMCAPAPY<br>VIDANAELIDRIAQEDMVRGVTIAAGGFFG<br>PQGRELRVPLADPKQNDKIEKFEYKGYKIT<br>NFEMESSALAGLSKLMGHKAMTVCMVIA<br>NRLIKEANTGYKNTIDTLIKTILDRI<br>as shown in SEQ ID NO. 4 |
| Example 4 | Q8ZJV7 | *Salmonella typhimurium* (ATCC 700720) | MATPHINAEMGDFADVVLMPGDPLRAKHI<br>AETFLENVREVNNVRGMLGFTGTYKGRKI<br>SVMGHGMGIPSCSIYTKELITDFGVKKIIRV<br>GSCGAVRMDVKLRDVVIGMGACTDSKVN<br>RIRFKDHDFAAIADFDMVRNAVDAAKAL<br>GVDARVGNLFSADLFYSPDGEMFDVMEK<br>YGVLGVEMEAAGIYGVAAEFGAKALTICT<br>VSDHIRTHEQTTAAERQTTFNDMIKIALES<br>VLLGDKE<br>as shown in SEQ ID NO. 5 |
| Example 5 | A0A4P7IUL0 | *Aeromonas hydrophila* | MQQDPVLNAVATILARKPGFAPRAAMILG<br>SGLGVLADGLEEKVTIPYEELDGFPVSTVA<br>GHSGELVLGKLHGVDVVCMKGRGHYYE<br>HETMKVMTTPVRTFKRLGCELLLVTNAA<br>GSLRPERIGVGSLVIFNDHINTMPGTPMTG<br>ANDEAYGPRFFSLANAYDKALRGEALALA<br>EREGIAVNQGVFVSYSGPCFETAAEIRMM<br>QIIGGDVVGMSVVPEVVSAAHCALPVLAI<br>CAITNMAEGLGDVQLSHEQTLKCAKLAET<br>DFIRLINAFIKHHFQ<br>as shown in SEQ ID NO. 6 |
| Example 6 | Q9RSF8 | *Deinococcus radiodurans* (strain ATCC 13939) | MDIGELFGLAHVHEQRPLLHQLLPFGGGD<br>FFHGGSIANPTEKKAGRAANRRKFGRNAL<br>RSPDTLRGMSIHLNAEKGQIAETVLLPGDP<br>LRARHIAETFLENPVQHNTVRGMLGFTGT<br>YKGERVSVQGTGMGIPSCMIYVNELIQDY<br>GCKNLIRVGTAGSYQEGVHVRDLVLAQA<br>ACTDSNINRVRFGERTFAPIADFELLLRAY<br>QIAQERGFSAHVGNIMSSDTFYNDNPTEFQ<br>RWAEFGVLAVEMEAAGLYTLAAKYGVR<br>ALTILTISDHLVTHEVTSAEERQLTFNGMIE<br>VALDAALGLEKKA<br>as shown in SEQ ID NO. 7 |
| Example 6 | LACC1 | *Homo sapiens* (Human) | MENEFTYEDYQRTAEWLRSHTKHRPQVA<br>VICGSGLGGLTAKLTQPQAFDYNEIPNFPQ<br>STVQGHAGRLVFGFLNGRSCVMMQGRFH<br>MYEGYSLSKVTFPVRVFHLLGVDTLVVTN<br>AAGGLNPKFEVGDIMLIRDHINLPGFCGQN<br>PLRGPNDERFGVRFPAMSDAYDRDMRQK<br>AFNAWKQMGEQRELQEGTYIMSAGPTFET<br>VAESCLLRMLGADAVGMSTVPEVIVARHC<br>GLRVFGFSLITNKVVMDYNNLEKASHQEV<br>LEAGKAAAQKLEQFVSILMESIPPRERAN<br>as shown in SEQ ID NO. 8 |

TABLE 2

| NRK enzyme sequence listing | | | |
|---|---|---|---|
| | UniprotID | Source | Gene sequence |
| Example 1 | P44308 | *Haemophilus influenzae* ATCC 51907 | MGFTTGREFHPALRMRAKYNAKYLGT<br>KSEREKYFHLAYNKHTQFLRYQEQIMS<br>KTKEKKVGVIFGKFYPVHTGHINMIYE<br>AFSKVDELHVIVCSDTVRDLKLFYDSK<br>MKRMPTVQDRLRWMQQIFKYQKNQIFI<br>HHLVEDGIPSYPNGWQSWSEAVKTLFH<br>EKHFEPSIVFSSEPQDKAPYEKYLGLEV<br>SLVDPDRTFFNVSATKIRTTPFQYWKFI<br>PKEARPFFAKTVAILGGESSGKSVLVNK<br>LAAVFNTTSAWEYGREFVFEKLGGDEQ<br>AMQYSDYPQMALGHQRYIDYAVRHSH<br>KIAFIDTDFITTQAFCIQYEGKAHPFLDS<br>MIKEYPFDVTILLKNNTEWVDDGLRSL<br>GSQKQRQQFQQLLKKLLDKYKVPYIEIE<br>SPSYLDRYNQVKAVIEKVLNEEEISELQ<br>NTTFPIKGTSQ<br>as shown in SEQ ID NO. 9 |
| Example 2 | P24518 | *Salmonella typhimurium* (strain ATCC 700720) | MSSFDYLKTAIKQQGCTLQQVADASG<br>MTKGYLSQLLNAKIKSPSAQKLEALHR<br>FLGEFPRRQKNIGVVFGKFYPLHTGHI<br>YLIQRACSQVDELHIIMGYDDTRDRGLF<br>EDSAMSQQPTVSDRLRWLLQTFKYQK<br>NIRIHAFNEEGMEPYPHGWDVWSNGIK<br>AFMAEKGIQPSWIYTSEEADAPQYLEHL<br>GIETVLVDPERTFMNISGAQIRENPFRY<br>WEYIPTEVKPFFVRTVAILGGESSGKST<br>LVNKLANIFNTTSAWEYGRDYVFSHLG<br>GDEMALQYSDYDKIALGHAQYIDFAVK<br>YANKVAFIDTDVFTTQAFCKKYEGREH<br>PFVQALIDEYRFDLVILLENNTPWVADG<br>LRSLGSSVDRKAFQNLLVEMLKENNIEF<br>VHVKEADYDGRFLRCVELVKEMMGEQ<br>G<br>as shown in SEQ ID NO. 10 |
| Example 3, 4 | Q63W44 | *B.pseudomallei* k96243 | MPEPGVGAHAGGLDADAALARFFVITG<br>GPGSGKSTLIDALEARGYARSHEAGRG<br>VIQDQVAIGGHALPWRDRAAFADMML<br>GWEMRSHHLARRARGPVFFDRGVPDVI<br>GYLKLSALPVPAHLVAAAERFRYRRDV<br>FIAPPWPEIYAQDAERRQDYAEAVRTY<br>GAMVDTYAACGYRLIELPASVDERCR<br>FVLDVVEAAAAV<br>as shown in SEQ ID NO. 11 |
| Example 5 | P53915 | *Saccharomyces cerevisiae* ATCC 204508 | MTSKKVILVALSGCSSSGKTTIAKLTAS<br>LFTKATLIHEDDFYKHDNEVPVDAKYN<br>IQNWDSPEALDFKLFGKELDVIKQTGKI<br>ATKLIHNNNVDDPFTKFHIDRQVWDEL<br>KAKYDSINDDKYEVVIVDGFMIFNNTGI<br>SKKFDLKILVRAPYEVLKKRRASRKGY<br>QTLDSFWVDPPYYFDEFVYESYRANHA<br>QLFVNGDVEGLLDPRKSKNIKEFINDDD<br>TPIAKPLSWVCQEILKLCKD<br>as shown in SEQ ID NO. 12 |
| Example 6 | P62511 | *Ashbya gossypii* (strain ATCC 10895) | MTSQLAGFKGTRGTLLVGIGGCSSSGKS<br>TIAKLAVQVLEDAVLVHQDDFYRHDDE<br>VPFDEEYQIGNWDVPEALDMAQFEREL<br>DHIRATGRPAAKLVHNGNIDDVGKFGIS<br>EEYLEELRRRYRGRISQPVVLVDGFML<br>YHDDKVAARFDCRLLVRAPYATMKAR<br>RASRGGYKTLDSFWQDPPFYFDKFVYK<br>SYAATHARLFRNCDVEDRLVAPDVQEI<br>YNGDEAQITCVLEQVLDAIAAAQC<br>as shown in SEQ ID NO. 13 |

The present invention will be further described below in conjunction with the examples.

Example 1

Source of PNP Enzyme: *Bos taurus* (Bovine)

Preparation source of NRK enzyme: *Haemophilus influenzae* (ATCC 51907)

PNP/NRK enzyme ratio 1:1, 37° C., pH 6.5. The substrate concentration of adenosine was 150 mM, the substrate concentration of nicotinamide was 150 mM, the substrate concentration of ATP was 150 mM, the concentration of magnesium ions was 20 mM, the concentration of phosphate salt was 20 mM, and the substrate conversion rate was 90%.

Preparation of PNP enzyme: The protein sequence of PNP enzyme derived from *Bos taurus* is shown in Table 1. The corresponding DNA gene sequence was synthesized in vitro by General Biological (AnHui) Co. Ltd. after codon optimization, digested with Nde I/Xho I (NEB Company), and linked to the pET28a plasmid (purchased from Addgene) digested with the same enzyme. The constructed plasmid was transformed into the *E. coli* BL (DE3) strain (Shanghai Weidi Biotech). The confirmed correct colony was inoculated into LB culture medium containing 100 μM kanamycin, wherein the LB medium comprised of 1% tryptone, 0.5% yeast powder, 1% NaCl, 1% dipotassium hydrogen phosphate, 1% potassium dihydrogen phosphate and 5% glycerol. When the cells grew to mid-to-late logarithmic phase, 0.2 mM isopropyl-β-D-thiogalactopyranoside (IPTG) was add to induce protein expression at 30° C. for 5 h, and then the wet cells were collected by centrifugation.

Preparation of NRK enzyme: The DNA of *Haemophilus influenzae* ATCC 51907 strain was extracted as a template to amplify the NadR gene fragment (genbank: NZ_CP009610.1) by PCR, wherein the NadR forward primer was F: 5'-catatgcgagctaagtataacgcaaaat-3', and the NadR reverse primer was R: 5'-ctcgagtcattgagatgtccctttt-ataggaaaggt-3', synthesized by Genewiz. The protein sequence corresponding to this gene fragment is shown in Table 1. The amplified gene was digested with Nde I/Xho I purchased from NEB Company and linked to the pET28a plasmid (purchased from Addgene) digested with the same enzyme. The constructed plasmid was transformed into *E. coli* BL21 (DE3) strain (Shanghai Weidi Biotech). The confirmed correct colony was inoculated into LB culture medium containing 100 μM kanamycin, wherein the LB medium comprised 1% tryptone, 0.5% yeast powder, 1% NaCl, 1% dipotassium hydrogen phosphate, 1% potassium dihydrogen phosphate and 5% glycerol. When the cells grew to mid-to-late logarithmic phase, 0.2 mM isopropyl-β-D-thiogalactopyranoside (IPTG) was add to induce protein expression at 30° C. for 5 h, and then the wet cells were collected by centrifugation.

100 g of wet cells of each of the above PNP enzyme and NRK enzyme was weighed, resuspended in 1000 ml of 20 mM, pH 7.5 Tris aqueous solution and crushed under high pressure to obtain crude enzyme liquids of PNP enzyme and NRK enzyme. The well-known methods for measuring the enzyme activity of PNP enzyme and NRK enzyme in the prior art were used, and the amount of enzyme required to convert 1 micromole of substrate within 1 minute under specific conditions is regarded as one activity unit (U). The enzyme activity of the PNP enzyme of the present invention is defined as: the amount of enzyme required to convert 1 micromole of adenosine into D-ribose-1-phosphate in 1 minute is one activity unit (U). The enzyme activity of the NRK enzyme of the present invention is defined as: the amount of enzyme required to convert 1 micromole of nicotinamide ribose into β-nicotinamide ribose mononucleotide in one minute is one activity unit (U). The enzyme activity of the above PNP crude enzyme liquid was measured to be 75 U/ml, and the NRK enzyme activity was 600 U/ml.

150 mM adenosine, 150 mM nicotinamide, 20 mM $MgCl_2$, 150 mM ATP, and 20 mM pH 8.0 PBS buffer were added in a 1 L reactor. The pH value was adjusted to 6.5, and the total volume of the reaction solution was 0.8 L. 32 ml of the above PNP crude enzyme liquid and 4 ml of the above NRK crude enzyme liquid were added and stirred at 37° C. for 8 h while maintaining pH 8.0 to generate 135 mM (45.1 g/L) NMN, with a substrate conversion rate of 90%. The reaction solution was filtered, separated by chromatography, concentrated for crystallization, and dried to obtain 27.1 g of pure NMN, with a purity of 99.2% and an NMR result of $^1H$ NMR (400 MHz, $D_2O$) δ 9.46 (s. 1H), 9.29 (d, J=5.9 Hz, 1H), 8.99 (d, J=7.9 Hz, 1H), 8.31 (L, J=7.1 Hz, 1H), 6.22 (d, J=5.1 Hz, 1H), 4.64 (s, 1H), 4.58-4.55 (m, 1H), 4.46-4.43 (m, 1H), 4.32-4.29 (m, 1H), 4.17-4.13 (m, 1H).

Example 2

Source of PNP enzyme 1: *Escherichia coli* (strain K12)

Source of PNP enzyme 2: *Bacillus clausii* (strain KSM-K16)

Source of NRK enzyme: *Salmonella typhimurium* (ATCC 700720)

PNP/NRK enzyme ratio 100:1, 35° C., pH 8.5. The substrate concentration of adenosine was 135 mM, the substrate concentration of nicotinamide was 135 mM, the substrate concentration of ATP was 135 mM, the concentration of magnesium ions was 200 mM, the concentration of Tris was 20 mM, and the substrate conversion rate was 92%.

Preparation of PNP enzyme 1: The protein sequence of PNP enzyme derived from *Escherichia coli* (strain K12) is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation.

Preparation of PNP enzyme 2: The protein sequence of PNP enzyme derived from *Acillus clausii* (strain KSM-K16) is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation.

Preparation of NRK enzyme: The protein sequence of NRK enzyme derived from *Salmonella typhimurium* (ATCC 700720) is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation.

100 g of wet cells of each of the above PNP enzyme 1, PNP enzyme 2 and NRK enzyme was weighed, resuspended in 1000 ml of 20 mM, pH 7.5 Tris aqueous solution and crushed under high pressure to obtain crude enzyme liquid of PNP enzyme 1, PNP enzyme 2 and NRK enzyme. The enzyme activity of the crude enzyme liquid of PNP enzyme 1 was measured to be 200 U/ml, the enzyme activity of the crude enzyme liquid of PNP enzyme 2 was measured to be 500 U/ml and the NRK enzyme activity was 50 U/ml.

135 mM adenosine, 135 mM nicotinamide, 200 mM $MgCl_2$, 135 mM ATP, and 20 mM Tris were added in a 1 L reactor. The pH value was adjusted to 8.5, and the total volume of the reaction solution was 0.8 L. 50 ml of the crude enzyme liquid of PNP enzyme 1, 30 ml of the crude enzyme liquid of PNP enzyme 2 and 5 ml of the NRK crude enzyme liquid were added and stirred at 35° C. for 24 h while maintaining pH 8.5 to generate 124.2 mM (45.1 g/L) NMN, with a substrate conversion rate of 92%. The reaction solution was filtered, separated by chromatography, concentrated for crystallization, and dried to obtain 28.2 g of pure NMN, with a purity of 99.3%.

Example 3

Source of PNP enzyme: *Bacteroides fragilis* (strain ATCC 25285)

Source of NRK enzyme: *B. pseudomallei* K96243

Immobilized enzyme form;

the ratio of PNP to NRK enzyme was 10:1.

PNP/NRK enzyme ratio 10:1, 40° C., pH 7.0. The substrate concentration of adenosine was 50 mM, the substrate concentration of nicotinamide was 50 mM, the substrate concentration of ATP was 80 mM, the concentration of manganese ions was 5 mM, the concentration of phosphate salt was 200 mM, and the substrate conversion rate was 91.1%.

Preparation of PNP enzyme: The protein sequence of PNP enzyme derived from *Bacteroides fragilis* (strain ATCC 25285) is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation.

Preparation of NRK enzyme: The protein sequence of NRK enzyme derived from *B. pseudomallei* K96243 is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation.

The collected bacterial cells containing PNP enzyme and NRK enzyme were mixed, crushed under high pressure, and centrifuged to collect the supernatant containing crude protein. The supernatant was purified using a nickel ion chelating affinity column (Yisheng Biotechnology) to obtain PNP pure enzyme liquid and NRK pure enzyme liquid. The enzyme activity of PNP pure enzyme liquid was 6800 U/ml, and the enzyme activity of NRK pure enzyme liquid was 6400 U/ml.

The obtained pure enzyme liquid was immobilized once with LX-1000EP epoxy resin (Sunresin, Xi'an), and the method was as follows. 100 ml of the above PNP pure enzyme liquid and 10 ml of NRK pure enzyme liquid were added to 1 L of potassium phosphate buffer (1M pH 7.5), mixed well, added with 80 g of LX-1000EP epoxy resin, stirred at room temperature for 8 h, filtered to remove the resin, washed three times with 25 mM pH 8.0 potassium phosphate buffer, and subjected to suction filtration to obtain the immobilized enzyme. The immobilized enzyme was measured to have a PNP enzyme activity of 800 U/g and an NRK enzyme activity of 80 U/g.

50 mM adenosine, 50 mM nicotinamide, 5 mM MnC12, 80 mM ATP, and 200 mM pH 7.0 PBS buffer were added in a 1 L reactor. The pH value was adjusted to 7.0, and the total volume of the reaction solution was 0.8 L. 20 g of the above immobilized enzyme was added and stirred at 40° C. for 8 h while maintaining pH 7.0 to generate 45.5 mM (15.2 g/L) NMN, with a substrate conversion rate of 91.1%. The reaction solution was filtered, separated by chromatography, concentrated for crystallization, and dried to obtain 9.12 g of pure NMN, with a purity of 99.2%.

Example 4

Source of PNP enzyme: *Salmonella typhimurium* (ATCC 700720);

Source of NRK enzyme: *B. pseudomallei* K96243 purified enzyme

PNP/NRK enzyme ratio 1:100, 35° C., pH 7.5. The substrate concentration of adenosine was 100 mM, the substrate concentration of nicotinamide was 100 mM, the substrate concentration of ATP was 100 mM, the concentration of magnesium ions was 20 mM, the concentration of phosphate salt was 5 mM, and the substrate conversion rate was 99%.

Preparation of PNP enzyme: The protein sequence of PNP enzyme derived from *Salmonella typhimurium* (ATCC 700720) is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation. PNP pure enzyme liquid was prepared according to the method of Example 3, and the enzyme activity of PNP pure enzyme liquid was 6200 U/ml.

100 mM adenosine, 100 mM nicotinamide, 20 mM $MgCl_2$, 100 mM ATP, and 20 mM pH 8.0 PBS buffer were added in a 1000 ml Erlenmeyer flask. The pH value was adjusted to 8.0, and the total volume of the reaction solution was 500 ml. 4.8 ml of the above PNP pure enzyme liquid and 46 ml of NRK pure enzyme liquid derived from *B. pseudomallei* K96243 were added and stirred at 35° C. for 24 h while maintaining pH 8.0 to generate 99 mM (30.07 g/L) NMN, with a substrate conversion rate of 99%. The reaction solution was filtered, separated by chromatography, concentrated for crystallization, and dried to obtain 12.7 g of pure NMN, with a purity of 99.4%.

Example 5

Source of PNP enzyme: *Aeromonas hydrophila*

Source of NRK enzyme: *Saccharomyces cerevisiae* ATCC 204508

Co-expression of NRK and PNP+ whole cell catalytic form (enzyme activity ratio 1:1) PNP/NRK enzyme ratio 1:1, 37° C., pH 8.0. The substrate concentration of adenosine was 135 mM, the substrate concentration of nicotinamide was 135 mM, the substrate concentration of ATP was 135 mM, the concentration of magnesium ions was 20 mM, the concentration of phosphate salt was 20 mM, and the substrate conversion rate was 92%. Whole cell preparation: The protein sequence of PNP enzyme derived from *Aeromonas hydrophila* is shown in Table 1. The corresponding DNA gene sequence was synthesized in vitro by General Biological (AnHui) Co. Ltd. after codon optimization, and digested with BamH I/Not I (NEB Company). The protein sequence of NRK enzyme derived from *Saccharomyces cerevisiae*

ATCC 204508 is shown in Table 1. The corresponding DNA gene sequence was synthesized in vitro by General Biological (AnHui) Co. Ltd. after codon optimization, and digested with BamH I/Not I (NEB Company). Both of the two genes digested above were linked to the pRSFDuet-1 plasmid (purchased from Biofeng) digested with the same enzyme. The constructed plasmid was transformed into the *E. coli* BL21 (DE3) strain (Shanghai Weidi Biotech). The confirmed correct colony was inoculated into LB culture medium containing 100 μM kanamycin, wherein the LB medium comprised 1% tryptone, 0.5% yeast powder, 1% NaCl, 1% dipotassium hydrogen phosphate, 1% potassium dihydrogen phosphate and 5% glycerol. When the cells grew to mid-to-late logarithmic phase, 0.2 mM isopropyl-β-D-thiogalactopyranoside (IPTG) was add to induce protein expression at 30° C. for 5 h, and then the wet cells were collected by centrifugation.

The wet cells after centrifugation were washed twice with 20 mM pH 7.0 PBS buffer, resuspended, added with 0.15% Triton X-100, stirred at low speed for 30 min, and then centrifuged to collect wet cells. The wet cells after permeabilization were measured to have a PNP enzyme activity of 750 U/g and an NRK enzyme activity of 750 U/g.

135 mM adenosine, 135 mM nicotinamide, 20 mM $MgCl_2$, 135 mM ATP, and 20 mM pH 8.0 PBS buffer were added in a 1 L reactor. The pH value was adjusted to 8.0, and the total volume of the reaction solution was 0.8 L. 32 g of the above wet cells was added and stirred at 37° C. for 12 h while maintaining pH 8.0 to generate 124.2 mM (41.48 g/L) of NMN, with a substrate conversion rate of 92%. The reaction solution was filtered, separated by chromatography, concentrated for crystallization, and dried to obtain 24.22 g of pure NMN, with a purity of 99.1%.

Example 6

Source of PNP enzyme 1: *Deinococcus radiodurans* (strain ATCC 13939)

Source of PNP enzyme 2: *Homo sapiens* (Human)

Source of NRK enzyme: *Ashbya gossypii* (strain ATCC 10895)

In this example, the effects of different forms of crude enzyme, pure enzyme, and immobilized enzyme with the same enzyme activity (1:0.518) were compared.

PNP enzyme 1/NRK enzyme ratio 1:0.518, crude enzyme, 37° C., pH 8.0. The substrate concentration of adenosine was 100 mM, the substrate concentration of nicotinamide was 100 mM, the substrate concentration of ATP was 100 mM, the concentration of magnesium ions was 20 mM, the concentration of phosphate salt was 20 mM, and the substrate conversion rate was 90%.

PNP enzyme 1/NRK enzyme ratio 1:0.518, pure enzyme, 37° C., pH 8.0. The substrate concentration of adenosine was 100 mM, the substrate concentration of nicotinamide was 100 mM, the substrate concentration of ATP was 100 mM, the concentration of magnesium ions was 20 mM, the concentration of phosphate salt was 20 mM, and the substrate conversion rate was 95%.

PNP enzyme 1/NRK enzyme ratio 1:0.518, immobilized enzyme, 37° C., pH 8.0. The substrate concentration of adenosine was 100 mM, the substrate concentration of nicotinamide was 100 mM, the substrate concentration of ATP was 100 mM, the concentration of magnesium ions was 20 mM, the concentration of phosphate salt was 20 mM, and the substrate conversion rate was 94%.

PNP enzyme 1/NRK enzyme ratio 1:0.518, immobilized enzyme, 25° C., pH 9.5. The substrate concentration of adenosine was 1 mM, the substrate concentration of nicotinamide was 1 mM, the substrate concentration of ATP was 1 mM, the concentration of magnesium ions was 1 mM, the concentration of phosphate salt was 5 mM, and the substrate conversion rate was 99%.

PNP enzyme 1/NRK enzyme ratio 1:0.518, immobilized enzyme, 45° C., pH 9.5. The substrate concentration of adenosine was 1 mM, the substrate concentration of nicotinamide was 1 mM, the substrate concentration of ATP was 1 mM, the concentration of magnesium ions was 1 mM, the concentration of phosphate salt was 5 mM, and the substrate conversion rate was 99%.

Preparation of PNP enzyme 1: The protein sequence of PNP enzyme derived from *Deinococcus radiodurans* (strain ATCC 13939) is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation.

Preparation of PNP enzyme 2: The protein sequence of PNP enzyme derived from *Homo sapiens* (Human) is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation.

Preparation of NRK enzyme: The protein sequence of NRK enzyme derived from *Ashbya gossypii* (strain ATCC 10895) is shown in Table 1. The corresponding DNA gene sequence was synthesized in vitro by General Biological (AnHui) Co. Ltd. after codon optimization. The construction of genetically recombinant bacteria and bacterial culture were performed according to the method of Example 1, and wet cells were collected by centrifugation.

100 g of the above PNP enzyme 1 wet cells, PNP enzyme 2 wet cells, and NRK enzyme wet cells was weighed respectively, resuspended in 1000 ml of 20 mM, pH 7.5 Tris aqueous solution and crushed under high pressure to obtain crude enzyme liquids of PNP enzyme and NRK enzyme. The enzyme activity of the crude enzyme liquid of PNP enzyme 1 was measured to be 450 U/ml, the enzyme activity of the crude enzyme liquid of PNP enzyme 2 was measured to be 550 U/ml, and the enzyme activity of the crude enzyme liquid of NRK enzyme was 760 U/ml.

The crude enzyme liquids of PNP enzyme 1 and NRK enzyme prepared according to the above method were centrifuged to collect the supernatant. The supernatants were purified using s nickel ion chelate affinity column (Yisheng Biotechnology) to obtain pure enzyme liquids of PNP enzyme 1 and NRK enzyme. The enzyme activity of pure enzyme liquid of PNP enzyme 1 was 4800 U/ml, and the enzyme activity of pure enzyme liquid of NRK enzyme was 6700 U/ml.

The pure enzyme liquids obtained above were immobilized once with LX-1000EP epoxy resin (Sunresin, Xi'an), and the method was as follows. 50 ml of the above pure enzyme liquid of PNP enzyme 1 and 40 ml of NRK pure enzyme liquid were added to 2 L of potassium phosphate buffer (1M pH 7.5), mixed well, added with 160 g of LX-1000EP epoxy resin, stirred at room temperature for 8 h, filtered to remove the resin, washed three times with 25 mM pH 8.0 potassium phosphate buffer, and subjected to suction filtration to obtain the immobilized enzyme. The immobilized enzyme was measured to have a PNP enzyme 1 activity of 98.4 U/g and an NRK enzyme activity of 190 U/g.

Crude enzyme form (PNP enzyme 1): 100 mM adenosine, 100 mM nicotinamide, 20 mM $MgCl_2$, 100 mM ATP, 20 mM pH 8.0 PBS buffer were added in a 1 L reactor. The pH value was adjusted to 8.0, and the total volume of the reaction solution was 0.8 L. 35 ml of the crude enzyme liquid of PNP enzyme 1 and 40 ml of the NRK crude enzyme liquid were added and stirred at 37° C. for 6 h while maintaining pH 8.0 to generate 90 mM (30.06 g/L) of NMN, with a substrate conversion rate of 90%. The reaction solution was filtered, separated by chromatography, concentrated for crystallization, and dried to obtain 18.04 g of pure NMN, with a purity of 99.1%.

Crude enzyme form (PNP enzyme 2): 100 mM adenosine, 100 mM nicotinamide, 20 mM $MgCl_2$, 100 mM ATP, 20 mM pH 8.0 PBS buffer were added in a 1 L reactor. The pH value was adjusted to 8.0, and the total volume of the reaction solution was 0.8 L. 28.8 ml of the crude enzyme liquid of PNP enzyme 2 and 40 ml of the NRK crude enzyme liquid prepared above were added and stirred at 37° C. for 6 h while maintaining pH 8.0 to generate 1 mM (0.33 g/L) of NMN, with a substrate conversion rate of 1%. The substrate conversion rate was too low for purification to obtain pure product.

The result data of the use of PNP enzyme 2, which can only complete the first step of the reaction but not the second step, showed that the reaction can only proceed to the first step and failed to continue or continued at an extremely low efficiency. This also demonstrates that the process of generating nicotinamide ribose requires a specific PNP enzyme.

Pure enzyme form (PNP enzyme 1): 100 mM adenosine, 100 mM nicotinamide, 20 mM $MgCl_2$, 100 mM ATP, 20 mM pH 8.0 PBS buffer were added in a 1 L reactor. The pH value was adjusted to 8.0, and the total volume of the reaction solution was 0.8 L. 3.28 ml of the pure enzyme liquid of PNP enzyme 1 and 4.53 ml of the NRK pure enzyme liquid were added and stirred at 37° C. for 5 h while maintaining pH 8.0 to generate 95 mM (31.73 g/L) of NMN, with a substrate conversion rate of 95%. The reaction solution was filtered, separated by chromatography, concentrated for crystallization, and dried to obtain 20.05 g of pure NMN, with a purity of 99.4%.

Immobilized enzyme form (PNP enzyme 1): 100 mM adenosine, 100 mM nicotinamide, 20 mM $MgCl_2$, 100 mM ATP, 20 mM pH 8.0 PBS buffer were added in a 1 L reactor. The pH value was adjusted to 8.0, and the total volume of the reaction solution was 0.8 L. 160 g of the immobilized enzyme of PNP enzyme 1 and NRK enzyme was added and stirred at 37° C. for 5.5 h while maintaining pH 8.0 to generate 94 mM (31.39 g/L) of NMN, with a substrate conversion rate of 94%. The reaction solution was filtered, separated by chromatography, concentrated for crystallization, and dried to obtain 19.8 g of pure NMN, with a purity of 99.4%.

Immobilized enzyme form (PNP enzyme 1, 25° C.): 1 mM adenosine, 1 mM nicotinamide, 5 mM $MgCl_2$, 1 mM ATP, 5 mM pH 8.0 PBS buffer were added in a 1 L reactor. The pH value was adjusted to 9.5, and the total volume of the reaction solution was 0.8 L. 160 g of the immobilized enzyme of PNP enzyme 1 and NRK enzyme was added and stirred at 25° C. for 5.5 h while maintaining pH 9.5 to generate 0.99 mM (0.33 g/L) of NMN, with a substrate conversion rate of 99%. The reaction solution was filtered, separated by chromatography, concentrated for crystallization, and dried to obtain 0.13 g of pure NMN, with a purity of 99.4%.

Immobilized enzyme form (PNP enzyme 1, 45° C.): 1 mM adenosine, 1 mM nicotinamide, 5 mM $MgCl_2$, 1 mM ATP, 5 mM pH 8.0 PBS buffer were added in a 1 L reactor. The pH value was adjusted to 9.5, and the total volume of the reaction solution was 0.8 L. 160 g of the immobilized enzyme of PNP enzyme 1 and NRK enzyme was added and stirred at 45° C. for 0.5 h while maintaining pH 9.5 to generate 0.99 mM (0.33 g/L) of NMN, with a substrate conversion rate of 97%. The reaction solution was filtered, separated by chromatography, concentrated for crystallization, and dried to obtain 0.13 g of pure NMN, with a purity of 99.4%.

The above are only preferred embodiments of the present invention. It should be noted that those skilled in the art can make several improvements and modifications without departing from the principles of the present invention, and these improvements and modifications should be regarded as the protection scope of the present invention.

The invention claimed is:

1. An enzyme composition for preparing β-nicotinamide mononucleotide, consisting of purine nucleoside phosphorylase with an EC number of EC 2.4.2.1 and nicotinamide riboside kinase with an EC number of EC 2.7.1.22; wherein, the purine nucleoside phosphorylase is a purine nucleoside phosphorylase having an amino acid sequence as shown in any one of SEQ ID NO: 1 to 7, and a combination thereof.

2. The enzyme composition according to claim 1, wherein the nicotinamide riboside kinase is derived from the group consisting of *B. pseudomallei, Ashbya gossypii, Haemophilus influenzae, Saccharomyces cerevisiae, Schizosaccharomyces pombe, Salmonella typhimurium, Cupriavidus metallidurans, Xanthomonas campestris* pv. *Campestris, Agrobacterium vitis, Pseudarthrobacter chlorophenolicus, Actinobacillus succinogenes, Homo sapiens, and a combination thereof.*

3. A method for synthesizing β-nicotinamide mononucleotide by enzymatic catalysis, comprising using adenosine, nicotinamide, ATP, an ion selected from the group consisting of Mg ion and Mn ion, and phosphate as raw materials, and synthesizing β-nicotinamide mononucleotide under enzymatic catalysis of the enzyme composition according to claim 1.

4. The method according to claim 3, further comprising a step of purifying β-nicotinamide mononucleotide, consisting of filtering, separating by chromatography, concentrating for crystallization, and drying to obtain pure β-nicotinamide mononucleotide.

* * * * *

SEQUENCE LISTING

```
<160> NUMBER OF SEQ ID NOS: 13

<210> SEQ ID NO 1
<211> LENGTH: 289
<212> TYPE: PRT
<213> ORGANISM: Artificial Sequence
<220> FEATURE:
<223> OTHER INFORMATION: a purine nucleoside phosphorylase derived from
      Bos taurus

<400> SEQUENCE: 1

Met Ala Asn Gly Tyr Thr Tyr Glu Asp Tyr Gln Asp Thr Ala Lys Trp
1               5                   10                  15

Leu Leu Ser His Thr Glu Gln Arg Pro Gln Val Ala Val Ile Cys Gly
            20                  25                  30

Ser Gly Leu Gly Gly Leu Val Asn Lys Leu Thr Gln Ala Gln Thr Phe
        35                  40                  45

Asp Tyr Ser Glu Ile Pro Asn Phe Pro Glu Ser Thr Val Pro Gly His
    50                  55                  60

Ala Gly Arg Leu Val Phe Gly Ile Leu Asn Gly Arg Ala Cys Val Met
```

-continued

```
65                  70                  75                  80

Met Gln Gly Arg Phe His Met Tyr Glu Gly Tyr Pro Phe Trp Lys Val
                85                  90                  95

Thr Phe Pro Val Arg Val Phe Arg Leu Leu Gly Val Glu Thr Leu Val
            100                 105                 110

Val Thr Asn Ala Ala Gly Gly Leu Asn Pro Asn Phe Glu Val Gly Asp
        115                 120                 125

Ile Met Leu Ile Arg Asp His Ile Asn Leu Pro Gly Phe Ser Gly Glu
    130                 135                 140

Asn Pro Leu Arg Gly Pro Asn Glu Glu Arg Phe Gly Val Arg Phe Pro
145                 150                 155                 160

Ala Met Ser Asp Ala Tyr Asp Arg Asp Met Arg Gln Lys Ala His Ser
                165                 170                 175

Thr Trp Lys Gln Met Gly Glu Gln Arg Glu Leu Gln Glu Gly Thr Tyr
            180                 185                 190

Val Met Leu Gly Gly Pro Asn Phe Glu Thr Val Ala Glu Cys Arg Leu
        195                 200                 205

Leu Arg Asn Leu Gly Ala Asp Ala Glu Gly Met Ser Thr Val Pro Glu
    210                 215                 220

Val Ile Val Ala Arg His Cys Gly Leu Arg Val Phe Gly Phe Ser Leu
225                 230                 235                 240

Ile Thr Asn Lys Val Ile Met Asp Tyr Glu Ser Gln Gly Lys Ala Asn
                245                 250                 255

His Glu Glu Val Leu Glu Ala Gly Lys Gln Ala Ala Gln Lys Leu Glu
            260                 265                 270

Gln Phe Val Ser Leu Leu Met Ala Ser Ile Pro Val Ser Gly His Thr
        275                 280                 285

Gly


<210> SEQ ID NO 2
<211> LENGTH: 277
<212> TYPE: PRT
<213> ORGANISM: Artificial Sequence
<220> FEATURE:
<223> OTHER INFORMATION: a purine nucleoside phosphorylase derived from
      E. coli

<400> SEQUENCE: 2

Met Ser Gln Val Gln Phe Ser His Asn Pro Leu Phe Cys Ile Asp Ile
1               5                   10                  15

Ile Lys Thr Tyr Lys Pro Asp Phe Thr Pro Arg Val Ala Phe Ile Leu
            20                  25                  30

Gly Ser Gly Leu Gly Ala Leu Ala Asp Gln Ile Glu Asn Ala Val Ala
        35                  40                  45

Ile Ser Tyr Glu Lys Leu Pro Gly Phe Pro Val Ser Thr Val His Gly
    50                  55                  60

His Ala Gly Glu Leu Val Leu Gly His Leu Gln Gly Val Pro Val Val
65                  70                  75                  80

Cys Met Lys Gly Arg Gly His Phe Tyr Glu Gly Arg Gly Met Thr Ile
                85                  90                  95

Met Thr Asp Ala Ile Arg Thr Phe Lys Leu Leu Gly Cys Glu Leu Leu
            100                 105                 110

Phe Cys Thr Asn Ala Ala Gly Ser Leu Arg Pro Glu Val Gly Ala Gly
        115                 120                 125

Ser Leu Val Ala Leu Lys Asp His Ile Asn Thr Met Pro Gly Thr Pro
```

-continued

```
    130                 135                 140

Met Val Gly Leu Asn Asp Asp Arg Phe Gly Glu Arg Phe Phe Ser Leu
145                 150                 155                 160

Ala Asn Ala Tyr Asp Ala Glu Tyr Arg Ala Leu Leu Gln Lys Val Ala
                165                 170                 175

Lys Glu Glu Gly Phe Pro Leu Thr Glu Gly Val Phe Val Ser Tyr Pro
            180                 185                 190

Gly Pro Asn Phe Glu Thr Ala Ala Glu Ile Arg Met Met Gln Ile Ile
        195                 200                 205

Gly Gly Asp Val Val Gly Met Ser Val Val Pro Glu Val Ile Ser Ala
    210                 215                 220

Arg His Cys Asp Leu Lys Val Val Ala Val Ser Ala Ile Thr Asn Met
225                 230                 235                 240

Ala Glu Gly Leu Ser Asp Val Lys Leu Ser His Ala Gln Thr Leu Ala
                245                 250                 255

Ala Ala Glu Leu Ser Lys Gln Asn Phe Ile Asn Leu Ile Cys Gly Phe
            260                 265                 270

Leu Arg Lys Ile Ala
        275


<210> SEQ ID NO 3
<211> LENGTH: 236
<212> TYPE: PRT
<213> ORGANISM: Artificial Sequence
<220> FEATURE:
<223> OTHER INFORMATION: a purine nucleoside phosphorylase derived from
      Bacillus clausii

<400> SEQUENCE: 3

Met Thr Glu Phe Lys Gln Thr Pro His Ile Asn Ala Lys Gly Glu Ile
1               5                   10                  15

Ala Glu Thr Val Leu Leu Pro Gly Asp Pro Leu Arg Ala Lys Phe Ile
            20                  25                  30

Ala Glu Arg Phe Leu Thr Asp Val Val Gln Phe Asn Ser Val Arg Asn
        35                  40                  45

Met Phe Gly Phe Thr Gly Thr Tyr Asn Gly Lys Arg Ile Ser Val Met
    50                  55                  60

Gly Thr Gly Met Gly Met Pro Ser Met Gly Ile Tyr Ser Tyr Glu Leu
65                  70                  75                  80

Ile His Val Phe Gly Val Lys Asn Leu Ile Arg Val Gly Ser Cys Gly
                85                  90                  95

Ala Leu Gln Asp Asp Leu Asn Leu Tyr Asp Val Ile Leu Gly Met Gly
            100                 105                 110

Ala Ser Thr Asn Ser Asn Tyr Val Asn Gln Tyr His Leu Pro Gly Thr
        115                 120                 125

Phe Ala Pro Leu Ala Ser Tyr Ser Leu Leu Glu Lys Ala Lys Lys Ala
    130                 135                 140

Ala Asp Glu Lys Gly Val Pro Val His Val Gly Asn Ile Leu Ser Ser
145                 150                 155                 160

Asp Thr Phe Tyr Asn Ala Asp Glu Asp Ala Ala Gly Lys Trp Arg Asp
                165                 170                 175

Met Gly Ile Leu Gly Ile Glu Met Glu Ala Ala Ala Leu Tyr Met Asn
            180                 185                 190

Ala Ala Gln Ala Gly Val Asn Ala Leu Cys Ile Leu Thr Val Ser Asp
        195                 200                 205
```

-continued

```
His Ile Phe Lys Glu Glu Glu Thr Thr Ala Glu Glu Arg Glu Thr Ser
    210                 215                 220

Phe Thr Asn Met Met Glu Ile Ala Leu Glu Leu Ala
225                 230                 235


<210> SEQ ID NO 4
<211> LENGTH: 292
<212> TYPE: PRT
<213> ORGANISM: Artificial Sequence
<220> FEATURE:
<223> OTHER INFORMATION: a purine nucleoside phosphorylase derived from
      Bacteroides fragilis

<400> SEQUENCE: 4

Met Lys Lys Tyr Phe Pro Ser Ser Glu Leu Ile Ile Asn Glu Asp Gly
1               5                   10                  15

Ser Val Phe His Leu His Val Lys Pro Glu Trp Leu Ala Asp Lys Val
            20                  25                  30

Ile Leu Val Gly Asp Pro Gly Arg Val Ala Leu Val Ala Ser His Phe
        35                  40                  45

Glu Asn Lys Glu Cys Glu Val Glu Ser Arg Glu Phe Lys Thr Val Thr
    50                  55                  60

Gly Thr Tyr Lys Gly Lys Arg Ile Thr Val Val Ser Thr Gly Ile Gly
65                  70                  75                  80

Cys Asp Asn Ile Asp Ile Val Val Asn Glu Leu Asp Ala Leu Ala Asn
                85                  90                  95

Ile Asp Phe Gln Thr Arg Glu Glu Lys Glu His Leu Arg Ser Leu Glu
            100                 105                 110

Leu Val Arg Ile Gly Thr Cys Gly Gly Leu Gln Pro Asn Thr Pro Val
        115                 120                 125

Gly Thr Phe Val Cys Ser Glu Lys Ser Ile Gly Phe Asp Gly Leu Leu
    130                 135                 140

Asn Phe Tyr Ala Gly Arg Asn Ala Val Cys Asp Leu Pro Phe Glu Arg
145                 150                 155                 160

Ala Phe Leu Asn His Met Gly Trp Ser Gly Asn Met Cys Ala Pro Ala
                165                 170                 175

Pro Tyr Val Ile Asp Ala Asn Ala Glu Leu Ile Asp Arg Ile Ala Gln
            180                 185                 190

Glu Asp Met Val Arg Gly Val Thr Ile Ala Ala Gly Gly Phe Phe Gly
        195                 200                 205

Pro Gln Gly Arg Glu Leu Arg Val Pro Leu Ala Asp Pro Lys Gln Asn
    210                 215                 220

Asp Lys Ile Glu Lys Phe Glu Tyr Lys Gly Tyr Lys Ile Thr Asn Phe
225                 230                 235                 240

Glu Met Glu Ser Ser Ala Leu Ala Gly Leu Ser Lys Leu Met Gly His
                245                 250                 255

Lys Ala Met Thr Val Cys Met Val Ile Ala Asn Arg Leu Ile Lys Glu
            260                 265                 270

Ala Asn Thr Gly Tyr Lys Asn Thr Ile Asp Thr Leu Ile Lys Thr Ile
        275                 280                 285

Leu Asp Arg Ile
    290


<210> SEQ ID NO 5
<211> LENGTH: 239
<212> TYPE: PRT
<213> ORGANISM: Artificial Sequence
```

-continued

<220> FEATURE:
<223> OTHER INFORMATION: a purine nucleoside phosphorylase derived from
Salmonella typhimurium

<400> SEQUENCE: 5

```
Met Ala Thr Pro His Ile Asn Ala Glu Met Gly Asp Phe Ala Asp Val
1               5                   10                  15

Val Leu Met Pro Gly Asp Pro Leu Arg Ala Lys His Ile Ala Glu Thr
            20                  25                  30

Phe Leu Glu Asn Val Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Arg
                85                  90                  95

Met Asp Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Val Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Val
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235
```

<210> SEQ ID NO 6
<211> LENGTH: 275
<212> TYPE: PRT
<213> ORGANISM: Artificial Sequence
<220> FEATURE:
<223> OTHER INFORMATION: a purine nucleoside phosphorylase derived from
Aeromonas hydrophila

<400> SEQUENCE: 6

```
Met Gln Gln Asp Pro Val Leu Asn Ala Val Ala Thr Ile Leu Ala Arg
1               5                   10                  15

Lys Pro Gly Phe Ala Pro Arg Ala Ala Met Ile Leu Gly Ser Gly Leu
            20                  25                  30

Gly Val Leu Ala Asp Gly Leu Glu Glu Lys Val Thr Ile Pro Tyr Glu
        35                  40                  45

Glu Leu Asp Gly Phe Pro Val Ser Thr Val Ala Gly His Ser Gly Glu
    50                  55                  60

Leu Val Leu Gly Lys Leu His Gly Val Asp Val Val Cys Met Lys Gly
65                  70                  75                  80

Arg Gly His Tyr Tyr Glu His Glu Thr Met Lys Val Met Thr Thr Pro
                85                  90                  95
```

```
Val Arg Thr Phe Lys Arg Leu Gly Cys Glu Leu Leu Leu Val Thr Asn
            100                 105                 110

Ala Ala Gly Ser Leu Arg Pro Glu Arg Ile Gly Val Gly Ser Leu Val
        115                 120                 125

Ile Phe Asn Asp His Ile Asn Thr Met Pro Gly Thr Pro Met Thr Gly
    130                 135                 140

Ala Asn Asp Glu Ala Tyr Gly Pro Arg Phe Phe Ser Leu Ala Asn Ala
145                 150                 155                 160

Tyr Asp Lys Ala Leu Arg Gly Glu Ala Leu Ala Leu Ala Glu Arg Glu
                165                 170                 175

Gly Ile Ala Val Asn Gln Gly Val Phe Val Ser Tyr Ser Gly Pro Cys
            180                 185                 190

Phe Glu Thr Ala Ala Glu Ile Arg Met Met Gln Ile Ile Gly Gly Asp
        195                 200                 205

Val Val Gly Met Ser Val Val Pro Glu Val Val Ser Ala Ala His Cys
    210                 215                 220

Ala Leu Pro Val Leu Ala Ile Cys Ala Ile Thr Asn Met Ala Glu Gly
225                 230                 235                 240

Leu Gly Asp Val Gln Leu Ser His Glu Gln Thr Leu Lys Cys Ala Lys
                245                 250                 255

Leu Ala Glu Thr Asp Phe Ile Arg Leu Ile Asn Ala Phe Ile Lys His
            260                 265                 270

His Phe Gln
        275


<210> SEQ ID NO 7
<211> LENGTH: 305
<212> TYPE: PRT
<213> ORGANISM: Artificial Sequence
<220> FEATURE:
<223> OTHER INFORMATION: a purine nucleoside phosphorylase derived from
      Deinococcus radiodurans

<400> SEQUENCE: 7

Met Asp Ile Gly Glu Leu Phe Gly Leu Ala His Val His Glu Gln Arg
1               5                   10                  15

Pro Leu Leu His Gln Leu Leu Pro Phe Gly Gly Gly Asp Phe Phe His
            20                  25                  30

Gly Gly Ser Ile Ala Asn Pro Thr Glu Lys Lys Ala Gly Arg Ala Ala
        35                  40                  45

Asn Arg Arg Lys Phe Gly Arg Asn Ala Leu Arg Ser Pro Asp Thr Leu
    50                  55                  60

Arg Gly Met Ser Ile His Leu Asn Ala Glu Lys Gly Gln Ile Ala Glu
65                  70                  75                  80

Thr Val Leu Leu Pro Gly Asp Pro Leu Arg Ala Arg His Ile Ala Glu
                85                  90                  95

Thr Phe Leu Glu Asn Pro Val Gln His Asn Thr Val Arg Gly Met Leu
            100                 105                 110

Gly Phe Thr Gly Thr Tyr Lys Gly Glu Arg Val Ser Val Gln Gly Thr
        115                 120                 125

Gly Met Gly Ile Pro Ser Cys Met Ile Tyr Val Asn Glu Leu Ile Gln
    130                 135                 140

Asp Tyr Gly Cys Lys Asn Leu Ile Arg Val Gly Thr Ala Gly Ser Tyr
145                 150                 155                 160

Gln Glu Gly Val His Val Arg Asp Leu Val Leu Ala Gln Ala Ala Cys
```

```
                165                 170                 175

Thr Asp Ser Asn Ile Asn Arg Val Arg Phe Gly Glu Arg Thr Phe Ala
            180                 185                 190

Pro Ile Ala Asp Phe Glu Leu Leu Leu Arg Ala Tyr Gln Ile Ala Gln
        195                 200                 205

Glu Arg Gly Phe Ser Ala His Val Gly Asn Ile Met Ser Ser Asp Thr
    210                 215                 220

Phe Tyr Asn Asp Asn Pro Thr Glu Phe Gln Arg Trp Ala Glu Phe Gly
225                 230                 235                 240

Val Leu Ala Val Glu Met Glu Ala Ala Gly Leu Tyr Thr Leu Ala Ala
                245                 250                 255

Lys Tyr Gly Val Arg Ala Leu Thr Ile Leu Thr Ile Ser Asp His Leu
            260                 265                 270

Val Thr His Glu Val Thr Ser Ala Glu Glu Arg Gln Leu Thr Phe Asn
        275                 280                 285

Gly Met Ile Glu Val Ala Leu Asp Ala Ala Leu Gly Leu Glu Lys Lys
    290                 295                 300

Ala
305


<210> SEQ ID NO 8
<211> LENGTH: 289
<212> TYPE: PRT
<213> ORGANISM: Artificial Sequence
<220> FEATURE:
<223> OTHER INFORMATION: a purine nucleoside phosphorylase derived from
      Homo sapiens

<400> SEQUENCE: 8

Met Glu Asn Glu Phe Thr Tyr Glu Asp Tyr Gln Arg Thr Ala Glu Trp
1               5                   10                  15

Leu Arg Ser His Thr Lys His Arg Pro Gln Val Ala Val Ile Cys Gly
            20                  25                  30

Ser Gly Leu Gly Gly Leu Thr Ala Lys Leu Thr Gln Pro Gln Ala Phe
        35                  40                  45

Asp Tyr Asn Glu Ile Pro Asn Phe Pro Gln Ser Thr Val Gln Gly His
    50                  55                  60

Ala Gly Arg Leu Val Phe Gly Phe Leu Asn Gly Arg Ser Cys Val Met
65                  70                  75                  80

Met Gln Gly Arg Phe His Met Tyr Glu Gly Tyr Ser Leu Ser Lys Val
                85                  90                  95

Thr Phe Pro Val Arg Val Phe His Leu Leu Gly Val Asp Thr Leu Val
            100                 105                 110

Val Thr Asn Ala Ala Gly Gly Leu Asn Pro Lys Phe Glu Val Gly Asp
        115                 120                 125

Ile Met Leu Ile Arg Asp His Ile Asn Leu Pro Gly Phe Cys Gly Gln
    130                 135                 140

Asn Pro Leu Arg Gly Pro Asn Asp Glu Arg Phe Gly Val Arg Phe Pro
145                 150                 155                 160

Ala Met Ser Asp Ala Tyr Asp Arg Asp Met Arg Gln Lys Ala Phe Asn
                165                 170                 175

Ala Trp Lys Gln Met Gly Glu Gln Arg Glu Leu Gln Glu Gly Thr Tyr
            180                 185                 190

Ile Met Ser Ala Gly Pro Thr Phe Glu Thr Val Ala Glu Ser Cys Leu
        195                 200                 205
```

-continued

```
Leu Arg Met Leu Gly Ala Asp Ala Val Gly Met Ser Thr Val Pro Glu
    210                 215                 220

Val Ile Val Ala Arg His Cys Gly Leu Arg Val Phe Gly Phe Ser Leu
225                 230                 235                 240

Ile Thr Asn Lys Val Val Met Asp Tyr Asn Asn Leu Glu Lys Ala Ser
                245                 250                 255

His Gln Glu Val Leu Glu Ala Gly Lys Ala Ala Ala Gln Lys Leu Glu
            260                 265                 270

Gln Phe Val Ser Ile Leu Met Glu Ser Ile Pro Pro Arg Glu Arg Ala
        275                 280                 285

Asn


<210> SEQ ID NO 9
<211> LENGTH: 421
<212> TYPE: PRT
<213> ORGANISM: Artificial Sequence
<220> FEATURE:
<223> OTHER INFORMATION: a purine nucleoside phosphorylase derived from
      Haemophilus influenzae

<400> SEQUENCE: 9

Met Gly Phe Thr Thr Gly Arg Glu Phe His Pro Ala Leu Arg Met Arg
1               5                   10                  15

Ala Lys Tyr Asn Ala Lys Tyr Leu Gly Thr Lys Ser Glu Arg Glu Lys
            20                  25                  30

Tyr Phe His Leu Ala Tyr Asn Lys His Thr Gln Phe Leu Arg Tyr Gln
        35                  40                  45

Glu Gln Ile Met Ser Lys Thr Lys Glu Lys Lys Val Gly Val Ile Phe
    50                  55                  60

Gly Lys Phe Tyr Pro Val His Thr Gly His Ile Asn Met Ile Tyr Glu
65                  70                  75                  80

Ala Phe Ser Lys Val Asp Glu Leu His Val Ile Val Cys Ser Asp Thr
                85                  90                  95

Val Arg Asp Leu Lys Leu Phe Tyr Asp Ser Lys Met Lys Arg Met Pro
            100                 105                 110

Thr Val Gln Asp Arg Leu Arg Trp Met Gln Gln Ile Phe Lys Tyr Gln
        115                 120                 125

Lys Asn Gln Ile Phe Ile His His Leu Val Glu Asp Gly Ile Pro Ser
    130                 135                 140

Tyr Pro Asn Gly Trp Gln Ser Trp Ser Glu Ala Val Lys Thr Leu Phe
145                 150                 155                 160

His Glu Lys His Phe Glu Pro Ser Ile Val Phe Ser Ser Glu Pro Gln
                165                 170                 175

Asp Lys Ala Pro Tyr Glu Lys Tyr Leu Gly Leu Glu Val Ser Leu Val
            180                 185                 190

Asp Pro Asp Arg Thr Phe Phe Asn Val Ser Ala Thr Lys Ile Arg Thr
        195                 200                 205

Thr Pro Phe Gln Tyr Trp Lys Phe Ile Pro Lys Glu Ala Arg Pro Phe
    210                 215                 220

Phe Ala Lys Thr Val Ala Ile Leu Gly Gly Glu Ser Ser Gly Lys Ser
225                 230                 235                 240

Val Leu Val Asn Lys Leu Ala Ala Val Phe Asn Thr Thr Ser Ala Trp
                245                 250                 255

Glu Tyr Gly Arg Glu Phe Val Phe Glu Lys Leu Gly Gly Asp Glu Gln
            260                 265                 270
```

-continued

```
Ala Met Gln Tyr Ser Asp Tyr Pro Gln Met Ala Leu Gly His Gln Arg
        275                 280                 285

Tyr Ile Asp Tyr Ala Val Arg His Ser His Lys Ile Ala Phe Ile Asp
    290                 295                 300

Thr Asp Phe Ile Thr Thr Gln Ala Phe Cys Ile Gln Tyr Glu Gly Lys
305                 310                 315                 320

Ala His Pro Phe Leu Asp Ser Met Ile Lys Glu Tyr Pro Phe Asp Val
                325                 330                 335

Thr Ile Leu Leu Lys Asn Asn Thr Glu Trp Val Asp Asp Gly Leu Arg
            340                 345                 350

Ser Leu Gly Ser Gln Lys Gln Arg Gln Gln Phe Gln Gln Leu Leu Lys
        355                 360                 365

Lys Leu Leu Asp Lys Tyr Lys Val Pro Tyr Ile Glu Ile Glu Ser Pro
    370                 375                 380

Ser Tyr Leu Asp Arg Tyr Asn Gln Val Lys Ala Val Ile Glu Lys Val
385                 390                 395                 400

Leu Asn Glu Glu Glu Ile Ser Glu Leu Gln Asn Thr Thr Phe Pro Ile
                405                 410                 415

Lys Gly Thr Ser Gln
            420


<210> SEQ ID NO 10
<211> LENGTH: 410
<212> TYPE: PRT
<213> ORGANISM: Artificial Sequence
<220> FEATURE:
<223> OTHER INFORMATION: a purine nucleoside phosphorylase derived from
      Salmonella typhimurium

<400> SEQUENCE: 10

Met Ser Ser Phe Asp Tyr Leu Lys Thr Ala Ile Lys Gln Gln Gly Cys
1               5                   10                  15

Thr Leu Gln Gln Val Ala Asp Ala Ser Gly Met Thr Lys Gly Tyr Leu
            20                  25                  30

Ser Gln Leu Leu Asn Ala Lys Ile Lys Ser Pro Ser Ala Gln Lys Leu
        35                  40                  45

Glu Ala Leu His Arg Phe Leu Gly Leu Glu Phe Pro Arg Arg Gln Lys
    50                  55                  60

Asn Ile Gly Val Val Phe Gly Lys Phe Tyr Pro Leu His Thr Gly His
65                  70                  75                  80

Ile Tyr Leu Ile Gln Arg Ala Cys Ser Gln Val Asp Glu Leu His Ile
                85                  90                  95

Ile Met Gly Tyr Asp Asp Thr Arg Asp Arg Gly Leu Phe Glu Asp Ser
            100                 105                 110

Ala Met Ser Gln Gln Pro Thr Val Ser Asp Arg Leu Arg Trp Leu Leu
        115                 120                 125

Gln Thr Phe Lys Tyr Gln Lys Asn Ile Arg Ile His Ala Phe Asn Glu
    130                 135                 140

Glu Gly Met Glu Pro Tyr Pro His Gly Trp Asp Val Trp Ser Asn Gly
145                 150                 155                 160

Ile Lys Ala Phe Met Ala Glu Lys Gly Ile Gln Pro Ser Trp Ile Tyr
                165                 170                 175

Thr Ser Glu Glu Ala Asp Ala Pro Gln Tyr Leu Glu His Leu Gly Ile
            180                 185                 190

Glu Thr Val Leu Val Asp Pro Glu Arg Thr Phe Met Asn Ile Ser Gly
        195                 200                 205
```

```
Ala Gln Ile Arg Glu Asn Pro Phe Arg Tyr Trp Glu Tyr Ile Pro Thr
    210                 215                 220

Glu Val Lys Pro Phe Phe Val Arg Thr Val Ala Ile Leu Gly Gly Glu
225                 230                 235                 240

Ser Ser Gly Lys Ser Thr Leu Val Asn Lys Leu Ala Asn Ile Phe Asn
                245                 250                 255

Thr Thr Ser Ala Trp Glu Tyr Gly Arg Asp Tyr Val Phe Ser His Leu
            260                 265                 270

Gly Gly Asp Glu Met Ala Leu Gln Tyr Ser Asp Tyr Asp Lys Ile Ala
        275                 280                 285

Leu Gly His Ala Gln Tyr Ile Asp Phe Ala Val Lys Tyr Ala Asn Lys
    290                 295                 300

Val Ala Phe Ile Asp Thr Asp Phe Val Thr Thr Gln Ala Phe Cys Lys
305                 310                 315                 320

Lys Tyr Glu Gly Arg Glu His Pro Phe Val Gln Ala Leu Ile Asp Glu
                325                 330                 335

Tyr Arg Phe Asp Leu Val Ile Leu Leu Glu Asn Asn Thr Pro Trp Val
            340                 345                 350

Ala Asp Gly Leu Arg Ser Leu Gly Ser Ser Val Asp Arg Lys Ala Phe
        355                 360                 365

Gln Asn Leu Leu Val Glu Met Leu Lys Glu Asn Asn Ile Glu Phe Val
    370                 375                 380

His Val Lys Glu Ala Asp Tyr Asp Gly Arg Phe Leu Arg Cys Val Glu
385                 390                 395                 400

Leu Val Lys Glu Met Met Gly Glu Gln Gly
                405                 410


<210> SEQ ID NO 11
<211> LENGTH: 200
<212> TYPE: PRT
<213> ORGANISM: Artificial Sequence
<220> FEATURE:
<223> OTHER INFORMATION: a purine nucleoside phosphorylase derived from
      B. pseudomallei

<400> SEQUENCE: 11

Met Pro Glu Pro Gly Val Gly Ala His Ala Gly Gly Leu Asp Ala Asp
1               5                   10                  15

Ala Ala Leu Ala Arg Phe Phe Val Ile Thr Gly Gly Pro Gly Ser Gly
            20                  25                  30

Lys Ser Thr Leu Ile Asp Ala Leu Glu Ala Arg Gly Tyr Ala Arg Ser
        35                  40                  45

His Glu Ala Gly Arg Gly Val Ile Gln Asp Gln Val Ala Ile Gly Gly
    50                  55                  60

His Ala Leu Pro Trp Arg Asp Arg Ala Ala Phe Ala Asp Met Met Leu
65                  70                  75                  80

Gly Trp Glu Met Arg Ser His His Leu Ala Arg Arg Ala Arg Gly Pro
                85                  90                  95

Val Phe Phe Asp Arg Gly Val Pro Asp Val Ile Gly Tyr Leu Lys Leu
            100                 105                 110

Ser Ala Leu Pro Val Pro Ala His Leu Val Ala Ala Ala Glu Arg Phe
        115                 120                 125

Arg Tyr Arg Arg Asp Val Phe Ile Ala Pro Pro Trp Pro Glu Ile Tyr
    130                 135                 140

Ala Gln Asp Ala Glu Arg Arg Gln Asp Tyr Ala Glu Ala Val Arg Thr
```

145 150 155 160

Tyr Gly Ala Met Val Asp Thr Tyr Ala Ala Cys Gly Tyr Arg Leu Ile
165 170 175

Glu Leu Pro Arg Ala Ser Val Asp Glu Arg Cys Arg Phe Val Leu Asp
180 185 190

Val Val Glu Ala Ala Ala Ala Val
195 200

<210> SEQ ID NO 12
<211> LENGTH: 240
<212> TYPE: PRT
<213> ORGANISM: Artificial Sequence
<220> FEATURE:
<223> OTHER INFORMATION: a purine nucleoside phosphorylase derived from Saccharomyces cerevisiae

<400> SEQUENCE: 12

Met Thr Ser Lys Lys Val Ile Leu Val Ala Leu Ser Gly Cys Ser Ser
1 5 10 15

Ser Gly Lys Thr Thr Ile Ala Lys Leu Thr Ala Ser Leu Phe Thr Lys
20 25 30

Ala Thr Leu Ile His Glu Asp Asp Phe Tyr Lys His Asp Asn Glu Val
35 40 45

Pro Val Asp Ala Lys Tyr Asn Ile Gln Asn Trp Asp Ser Pro Glu Ala
50 55 60

Leu Asp Phe Lys Leu Phe Gly Lys Glu Leu Asp Val Ile Lys Gln Thr
65 70 75 80

Gly Lys Ile Ala Thr Lys Leu Ile His Asn Asn Asn Val Asp Asp Pro
85 90 95

Phe Thr Lys Phe His Ile Asp Arg Gln Val Trp Asp Glu Leu Lys Ala
100 105 110

Lys Tyr Asp Ser Ile Asn Asp Asp Lys Tyr Glu Val Val Ile Val Asp
115 120 125

Gly Phe Met Ile Phe Asn Asn Thr Gly Ile Ser Lys Lys Phe Asp Leu
130 135 140

Lys Ile Leu Val Arg Ala Pro Tyr Glu Val Leu Lys Lys Arg Arg Ala
145 150 155 160

Ser Arg Lys Gly Tyr Gln Thr Leu Asp Ser Phe Trp Val Asp Pro Pro
165 170 175

Tyr Tyr Phe Asp Glu Phe Val Tyr Glu Ser Tyr Arg Ala Asn His Ala
180 185 190

Gln Leu Phe Val Asn Gly Asp Val Glu Gly Leu Leu Asp Pro Arg Lys
195 200 205

Ser Lys Asn Ile Lys Glu Phe Ile Asn Asp Asp Asp Thr Pro Ile Ala
210 215 220

Lys Pro Leu Ser Trp Val Cys Gln Glu Ile Leu Lys Leu Cys Lys Asp
225 230 235 240

<210> SEQ ID NO 13
<211> LENGTH: 241
<212> TYPE: PRT
<213> ORGANISM: Artificial Sequence
<220> FEATURE:
<223> OTHER INFORMATION: a purine nucleoside phosphorylase derived from Ashbya gossypii

<400> SEQUENCE: 13

Met Thr Ser Gln Leu Ala Gly Phe Lys Gly Thr Arg Gly Thr Leu Leu

-continued

```
1               5                   10                  15

Val Gly Ile Gly Gly Cys Ser Ser Ser Gly Lys Ser Thr Ile Ala Lys
            20                  25                  30

Leu Ala Val Gln Val Leu Glu Asp Ala Val Leu Val His Gln Asp Asp
        35                  40                  45

Phe Tyr Arg His Asp Asp Glu Val Pro Phe Asp Glu Glu Tyr Gln Ile
    50                  55                  60

Gly Asn Trp Asp Val Pro Glu Ala Leu Asp Met Ala Gln Phe Glu Arg
65                  70                  75                  80

Glu Leu Asp His Ile Arg Ala Thr Gly Arg Pro Ala Ala Lys Leu Val
                85                  90                  95

His Asn Gly Asn Ile Asp Asp Val Gly Lys Phe Gly Ile Ser Glu Glu
            100                 105                 110

Tyr Leu Glu Glu Leu Arg Arg Arg Tyr Arg Gly Arg Ile Ser Gln Pro
        115                 120                 125

Val Val Leu Val Asp Gly Phe Met Leu Tyr His Asp Asp Lys Val Ala
    130                 135                 140

Ala Arg Phe Asp Cys Arg Leu Leu Val Arg Ala Pro Tyr Ala Thr Met
145                 150                 155                 160

Lys Ala Arg Arg Ala Ser Arg Gly Gly Tyr Lys Thr Leu Asp Ser Phe
                165                 170                 175

Trp Gln Asp Pro Pro Phe Tyr Phe Asp Lys Phe Val Tyr Lys Ser Tyr
            180                 185                 190

Ala Ala Thr His Ala Arg Leu Phe Arg Asn Cys Asp Val Glu Asp Arg
        195                 200                 205

Leu Val Ala Pro Asp Val Gln Glu Ile Tyr Asn Gly Asp Glu Ala Gln
    210                 215                 220

Ile Thr Cys Val Leu Glu Gln Val Leu Asp Ala Ile Ala Ala Ala Gln
225                 230                 235                 240

Cys
```